US00PP25946P3

(12) United States Plant Patent
Olesen

(10) Patent No.: US PP25,946 P3
(45) Date of Patent: Sep. 29, 2015

(54) MINIATURE ROSE PLANT NAMED 'POULPAH065'

(50) Latin Name: ***Rosa* hybrid**
Varietal Denomination: Poulpah065

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 167 days.

(21) Appl. No.: 13/986,915

(22) Filed: Jun. 14, 2013

(65) Prior Publication Data

US 2014/0373210 P1 Dec. 18, 2014

(51) Int. Cl.
*A01H 5/02* (2006.01)

(52) U.S. Cl.
USPC ..... Plt./119

(58) Field of Classification Search
USPC ..... Plt./101, 116, 119
See application file for complete search history.

(56) References Cited

PUBLICATIONS

UPOV-PLUTO Plant Variety Database, International Union for Protection of New Varieties of Plants, Jan. 19, 2015, obtained for cultiver 'Poulpah065' (1 page total).*
'HelpMeFind' website for roses, clematis and peonies. Cultivar 'Poulpah065'. Retrieved from the Internet http://www.helpmefind.com/rose/pl.php?n=88787 (1 page total).*
"Poulsen Roser A/S" catalog; Retrieved from the Internet http://www.poulsenroser.com (1 page total).*
"floradania.dk—New plants from Denmark, 2010" catalog, cited 'Poulpah065' (2 pages total).*

* cited by examiner

*Primary Examiner* — Susan McCormick Ewoldt

(57) ABSTRACT

A new miniature rose plant that has abundant, orange flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpah065'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulpah065', originated as a single seedling from the stated cross.

The new variety may be distinguished from its male pollen parent and female seed parent by the following characteristics. The upper surface of the flower petals, on the female seed parent are Orange Red Group 32C while the claimed variety has a petal upper surface which is predominantly Orange-Red Group 31B. The male pollen plant has a flower color general tonality which is in the Yellow-Orange Group while the claimed plant is in the Red Group.

The objective of the hybridization of this rose variety for commercial culture was to create a new and distinct variety with unique qualities, such as:

1. Uniform and abundant orange flowers;
2. Vigorous and compact growth;
3. Year-round flowering under glasshouse conditions;

4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpah065' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpah065' was selected by the inventor as a single plant from the progeny of the hybridization in 2007.

Asexual reproduction of 'Poulpah065' by cuttings was first done by Mogens N. Olesen in the nursery in Fredensborg, Denmark in 2008. This initial and other subsequent propagations conducted in controlled environments have demonstrated that the characteristics of 'Poulpah065' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpah065'. Specifically illustrated in the drawing are flowers at various stages of development, flower in parts, leaves, and stems. Illustrated plants are 3 months of age.

DETAILED DESCRIPTION OF THE VARIETY

The following is a description of 'Poulpah065', as observed in its growth in glasshouses Half Moon Bay, Calif. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulfiry', U.S. Plant Pat. No. 12,484. are compared to 'Poulpah065' in Chart 1.

CHART 1

| | 'Poulpah065' | 'Poulfiry' |
|---|---|---|
| Petalage: | 45 to 50 petals total, 10 o fwhich are petaloids | 20-25 petals |
| Flower Diameter: | 60 mm | 35-40 mm |
| General Tonality of Flower Color: | blend of Red Group 33B and Red Group 41B | Red Group 40B-40C |

FLOWER AND FLOWER BUD

Blooming habit: Continuous.

Flower bud:

*Size.*—Upon opening, 21 mm in length from base of receptacle to end of bud. 13 mm in diameter.

*Bud form.*—Urceolate.

*Bud color.*—As sepals unfold, petals are Red Group 53A with intonations of Red Group 53B and Orange-Red Group 34A.

*Sepals.*—Upper Surface: Color: Green Group 138B. Texture: Smooth, strongly pubescent. Lower Surface: Color: Green Group 138A. Texture: Smooth. Shape: Apex: Cirrhose. Base: Flat at union with receptacle. Margins: Margins have strong foliaceous appendages on three of the five sepals. Size: 25 mm long by 10 mm wide.

*Receptacle.*—Surface Texture: Smooth. Shape: Campanulate. Size: 8 mm tall and 8 mm wide. Color: Yellow Green Group 146C.

*Pedicel.*—Surface: Smooth. Length: 15 mm on average. Diameter: Generally 2 mm. Color: Yellow Green Group 146C. Strength: Strong.

*Borne.*—Singly.

Flower bloom:

*Fragrance.*—Light floral scent.

*Duration.*—As a pot plant, flowers last up to 28 days.

*Size.*—Flower diameter is 60 mm when open. Flower depth is 25 mm.

*Form.*—Generally flowers are cup shaped with a loose outer whorl of petals and a closed center.

*Shape of flower, side view.*—The upper portion is flat. The lower portion concave.

Petalage: Under normal conditions, flowers have 45 to 50 petals total, 10 of which are petaloids.

Color:

*General tonality.*—On open flower, a blend of Red Group 33B and Red Group 41B. General tonality changes to

*Upon opening, petals.*—Outermost petals are Orange-Red Group 32A on the upper surface splashed with Yellow-Orange Group 14B emanating from the base of the petal. The lower surface is Yellow-Orange Group 14B at the base of the petal. Orange-Red Group 35A splashed with Red Group 43B at the middle and marginal zone. The lower surface occasionally has intonations of Orange-Red Group N34A. Innermost petals are Orange-Red Group 33B shaded with Yellow-Orange Group 15A on the upper surface. Orange-Red Group 35A on the lower surface. At the base of the petal, the upper surface and under surface are Yellow Group 12A.

*After opening, petals.*—Outermost petals are Orange-Red Group 31B shaded with intonations of Orange-Red Group N34C on the upper surface. At the base of the upper surface a petal spot the color of Yellow-Orange Group 14A. Primarily Orange-Red Group 35A on the lower surface with intonations of Red Group 39A. At the base of the petal underside is Yellow Group 13B. Innermost petals are Orange Group 24B on the upper surface splashed with Yellow-Orange Group 15A. At the base is a petal spot Yellow-Orange Group 15A. Orange-Red Group 31B with streaks of Yellow-Orange Group 16C on the lower surface.

Petals:

*Petal reflex.*—Slight to none.

*Margin.*—Entire, with a slight point at the center, with moderate undulations.

*Shape.*—Generally rounded. Apex shape: Cuspidate. Base shape: Rounded.

*Size.*—30 mm (l) by 32 mm (w).

*Texture.*—Smooth.

*Thickness.*—Average.

Petaloids:

*Quantity.*—10 on average.

*Shape.*—The apex is round and base is acute.

*Color.*—Upper surface is Orange Group 24A blended with Yellow-Orange Group 15A. Lower surface is Orange Group 24C streaked with Yellow-Orange Group 16B. Size: 20 mm (l) by 15 mm (w).

Reproductive organs:

*Pollen.*—None Observed.

*Anthers.*—Size: 2 mm long. Color: Yellow Group 13A. Quantity: 35 on average.

*Filaments.*—Color: Yellow Group 14A. Length: About 4 mm.

*Pistils.*—Length: About 8 mm long. Quantity: 25 on average.

*Stigmas.*—Superior relative to the length of the filaments and the height of the anthers. Color: Yellow Group 3D.

*Styles.*—Color: Yellow Group 4C.

*Seed formation.*—Not observed.

PLANT

Plant growth: Upright. Plants are 18 cm in height, and 15 cm wide.

Stems:

*Color*.—Juvenile growth: Yellow-Green Group 146D with anthocyanin the color of Greyed-Orange Group 176C. Mature growth: Yellow-Green Group 146B.

*Length*.—Canes are 11 cm from the base of the plant to the flowering portion.

*Diameter*.—3 mm.

*Internodes*.—On mature canes, there is an average distance of 20 mm between nodes.

*Surface texture*.—Young and mature wood is smooth.

Prickles:

*Incidence*.—3 to 4 per 10 cm of stem.

*Size*.—Average length: 6 mm.

*Color*.—Juvenile and mature prickles are Greyed-Purple Group 184B.

*Shape*.—Linear.

Plant foliage:

*Compound leaf size*.—70 mm (l) by 53 mm (w).

*Leaf bearing angle to the stem*.—90 degrees.

*Quantity*.—4 leaves per 10 cm of stem.

*Color of juvenile foliage*.—Upper Leaf Surface: Yellow-Green Group 144A with anthocyanin at the margins Greyed-Red Group 178A. Lower Leaf Surface: Yellow-Green Group 144B shaded with Greyed-Red Group 181A.

*Color of mature foliage*.—Upper Leaf Surface: Yellow-Green Group 147A with anthocyanin occasionally at margins Greyed-Purple Group 187A. Lower Leaf Surface: Green Group 138B.

Plant leaves and leaflets:

*Stipules*.—Size: About 8 mm in length. Shape: Linear, slightly broad based with outward extending apecies. Margins: Finely serrated with few stipitate glands. Color: Yellow-Green Group 144A.

*Petiole*.—Length: 11 mm on average. Diameter: About 1 mm. Upper surface: Yellow-Green Group 144B with Greyed-Purple Group 183B. Lower surface: Yellow-Green Group 144B.

*Rachis*.—Length: 18 mm on average. Diameter: About 1 mm. Upper surface: Yellow-Green Group 144B with Greyed-Purple Group 183B. Lower surface: Yellow-Green Group 144B.

Leaflet:

*Number of leaflets*.—5 on normal leaves in middle of the stem.

*Size*.—40 mm in length by 26 mm wide.

*Margin*.—Serrate.

*General shape*.—Elliptical.

*Apex shape*.—Acute.

*Base shape*.—Round.

*Texture*.—Smooth.

*Arrangement*.—Odd pinnate.

*Venation*.—Reticulate.

*Leaf gloss*.—Glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpah065', substantially as illustrated and described herein, due to its abundant, orange flowers, vigorous growth, compact habit, suitability for production from softwood cuttings in pots, and durable flowers and foliage that make the variety suitable for distribution in the floral industry.

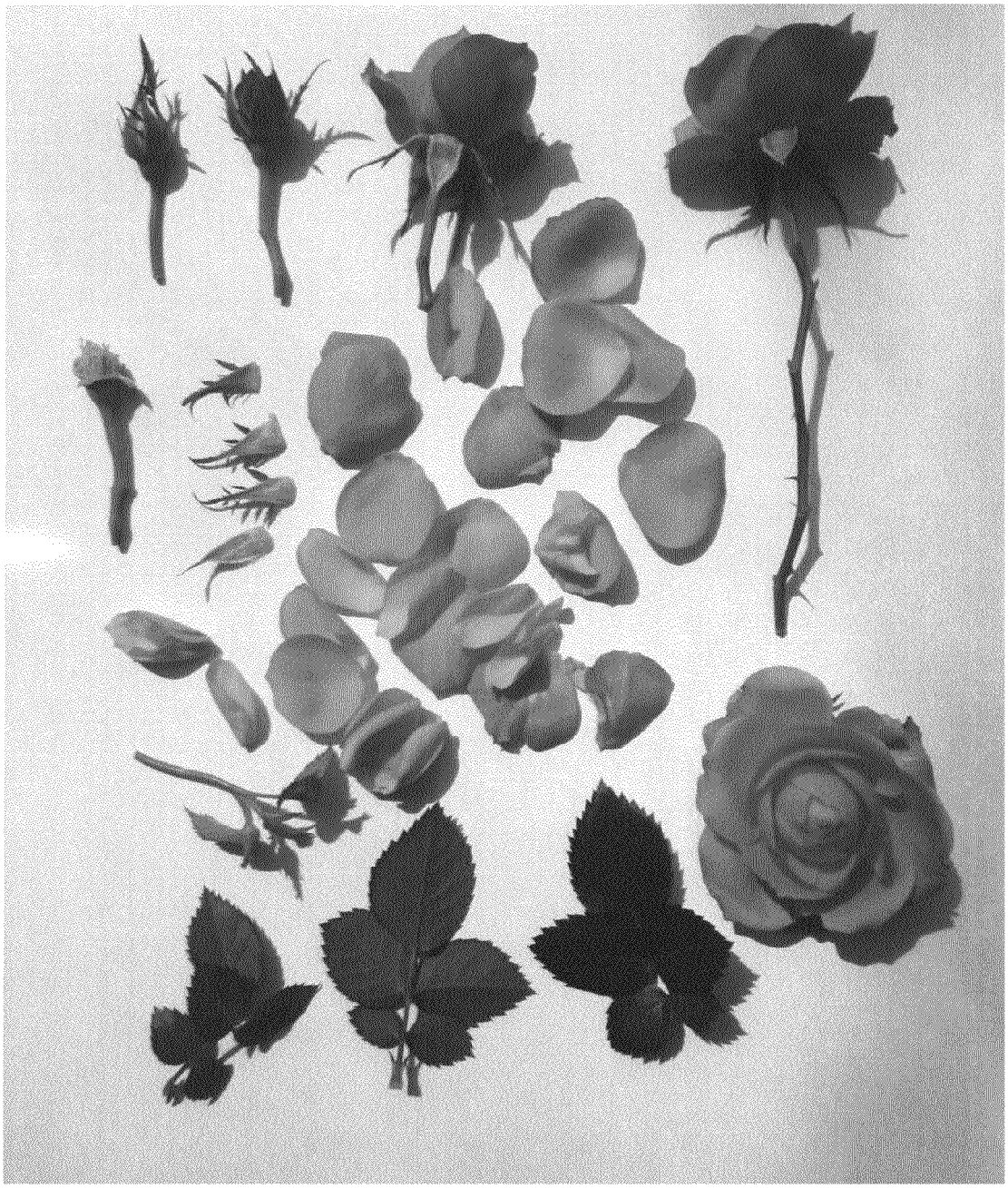

* * * * *